(12) United States Patent
Ziaie et al.

(10) Patent No.: US 9,962,084 B2
(45) Date of Patent: May 8, 2018

(54) WIRELESS INTERSTITIAL FLUID PRESSURE SENSOR

(71) Applicant: Purdue Research Foundation, West Lafayette, IN (US)

(72) Inventors: Babak Ziaie, West Lafayette, IN (US); Marcus Anthony Brown, Chicago, IL (US); Teimour Maleki-Jafarabadi, Thousand Oaks, CA (US); Seung Hyun Song, St. Louis, MO (US)

(73) Assignee: PURDUE RESEARCH FOUNDATION, West Lafayette, IN (US)

( * ) Notice: Subject to any disclaimer, the term of this patent is extended or adjusted under 35 U.S.C. 154(b) by 236 days.

(21) Appl. No.: 14/305,907

(22) Filed: Jun. 16, 2014

(65) Prior Publication Data

US 2014/0371624 A1   Dec. 18, 2014

Related U.S. Application Data

(60) Provisional application No. 61/835,536, filed on Jun. 15, 2013.

(51) Int. Cl.
*A61B 5/00* (2006.01)
*A61B 5/03* (2006.01)

(52) U.S. Cl.
CPC .......... *A61B 5/0031* (2013.01); *A61B 5/036* (2013.01)

(58) Field of Classification Search
CPC ......... A61B 5/0031; A61B 5/03; A61B 5/031; A61B 5/036; G01F 15/066; G01L 9/007;
(Continued)

(56) References Cited

U.S. PATENT DOCUMENTS 6,764,446 B2 * 7/2004 Wolinsky ............. A61B 5/0028
600/300
7,146,861 B1 * 12/2006 Cook .................... A61B 5/0215
73/715

(Continued)

OTHER PUBLICATIONS

A. C. Guyton, J. Prather, K. Scheel, and J. McGehee,"Interstitial Fluid Pressure," Circulation Research, 1966, 19, 1022-1030.
(Continued)

*Primary Examiner* — Michael C Stout
(74) *Attorney, Agent, or Firm* — Purdue Research Foundation (57) ABSTRACT

An implantable pressure sensor arrangement is disclosed. The arrangement includes a substrate, a coil positioned on the substrate, a flexible membrane positioned proximate to the coil and configured to be moveable with respect to the coil, thereby forming a fluid chamber, fluidly sealed from outside of the implantable pressure sensor arrangement, a porous membrane positioned on the flexible membrane and configured to transfer pressure from outside of the implantable pressure sensor arrangement onto the flexible membrane wherein a differential pressure is generated on the two sides of the flexible membrane thereby causing the flexible membrane to deflect towards and away from the coil, and an electrode coupled to the flexible membrane.

18 Claims, 9 Drawing Sheets

(58) Field of Classification Search
CPC ....... G01L 9/0072–9/0073; G01L 9/10–9/105; G01L 9/12
See application file for complete search history.

(56) References Cited

U.S. PATENT DOCUMENTS

| | | | | |
|---|---|---|---|---|
| 7,181,975 | B1* | 2/2007 | Bradley | G01L 9/0072 361/283.1 |
| 7,574,792 | B2* | 8/2009 | O'Brien | A61B 5/0031 29/600 |
| 7,785,268 | B2* | 8/2010 | Miethke | A61B 5/0031 600/561 |
| 7,900,518 | B2* | 3/2011 | Tai | A61B 3/16 361/283.4 |
| 8,506,514 | B2* | 8/2013 | Pedersen | A61B 5/031 604/6.16 |
| 2002/0151816 | A1* | 10/2002 | Rich | A61B 5/0031 600/547 |
| 2004/0057589 | A1* | 3/2004 | Pedersen | G01L 9/0073 381/152 |
| 2005/0266582 | A1* | 12/2005 | Modlin | B01L 3/502723 436/164 |
| 2006/0117859 | A1* | 6/2006 | Liu | A61B 5/02152 73/753 |
| 2007/0074579 | A1* | 4/2007 | Cook | G01L 9/0072 73/718 |
| 2009/0143696 | A1* | 6/2009 | Najafi | A61B 5/0031 600/561 |
| 2009/0155918 | A1* | 6/2009 | Payen | A61B 5/14539 436/149 |
| 2009/0299216 | A1* | 12/2009 | Chen | A61B 3/16 600/561 |
| 2010/0030103 | A1* | 2/2010 | Lutze | A61B 5/0008 600/561 |
| 2010/0161004 | A1* | 6/2010 | Najafi | A61N 1/3787 607/60 |
| 2012/0302861 | A1* | 11/2012 | Marshall | A61B 3/16 600/398 |
| 2014/0061892 | A1* | 3/2014 | Ziglioli | B81B 7/0058 257/704 |

OTHER PUBLICATIONS

C.-H. Heldin, K. Rubin, K. Pietras, and A. Östman, "High interstitial fluid pressure-an obstacle in cancer therapy," Nature Reviews Cancer, 2004, 4, 806-813.
L. H. Reddy, "Drug Delivery to Tumors: Recent Strategies," J. Pharm. Pharmacol., 2005, 57, 1231-42.
M. C. McGee, et al. "Improved Intratumoral Oxygenation through Vascular Normalization Increases Glioma Sensitivity to Ionizing Radiation," Int J Radiat Oncol Biol Phys., 2010, 76, 1537-45.
M. I. Lin, W. C. Sessa, "Antiangiogenic Therapy: Creating a Unique "Window" of Opportunity," Cancer Cell, 2004, 6, 529-31.
H. Wiig, "Evaluation of Methodologies for Measurement of Interstitial Fluid Pressure," Critical Reviews in Biomedical Engineering, 1990, 18, 27-54.
C. Guyton, "A Concept of Negative Interstitial Pressure Based on Pressures in Implanted Perforated Capsules," Circulation Research, 1963, 12, 399-414.
C. Neugebauer, "Saturation Magnetization of Nickel Films of Thickness Less Than 100 A," Physical Review, 1959, 116, 1441-1446.
G. Rado and A. Kaufmann, "Absolute Saturation Magnetization of Nickel-Antimony and Nickel-Tantalum Alloys," Physical Review, 1941, 60, 336-339.

* cited by examiner

WIRELESS INTERSTITIAL FLUID PRESSURE SENSOR

CROSS-REFERENCE TO RELATED APPLICATIONS

The present U.S. patent application is related to and claims the priority benefit of U.S. Provisional Patent Application Ser. No. 61/835,536, filed Jun. 15, 2013, the contents of which are hereby incorporated by reference in its entirety into the present disclosure.

STATEMENT REGARDING GOVERNMENT FUNDING

This invention was made with government support under EB013486 and EB007256 awarded by The National Institutes of Health. The government has certain rights in the invention.

TECHNICAL FIELD

This application relates to systems, methods and approaches to wirelessly measure interstitial fluid pressure.

BACKGROUND

This section introduces aspects that may help facilitate a better understanding of the disclosure. Accordingly, these statements are to be read in this light and are not to be understood as admissions about what is or is not prior art.

Interstitial fluid pressure (IFP) is a major governing parameter in oxygen, nutrients, and waste product exchange between capillary bed and the tissue interstitial space. In normal tissues, the interstitial fluid pressure is slightly negative (−1 mmHg to −6 mmHg), promoting the diffusion of nutrients into the tissue. IFP is also an important clinical parameter in cancer chemo and radiation therapeutics. Irregular vasculatures of tumors can result in abnormally high IFP (as high as 60 mmHg), limiting the delivery of chemotherapeutics and oxygen, both crucial elements in successful therapy.

There are several methods to measure interstitial fluid pressure in acute settings. These include micro-capillary, wick-in-needle, and fiber optic pressure sensor. These are not suitable for continuous chronic measurements desirable in therapeutic scenarios. One method first proposed by Guyton uses a perforated capsule implanted subcutaneously for measurement of IFP. This method allows for an accurate IFP measurement by permitting the interstitial liquid to fill the capsule (without interference from various cellular components) after implantation. After several weeks, the IFP is measured by insertion of a hypodermic needle, connected to an external pressure sensor, into the capsule. Tumors exhibit increased IFP (as high as 60 mmHg), poor blood circulation, and unbalanced interstitial fluid chemistry. Many factors contribute to the rise of IFP in tumor tissues. Blood vessels are extremely defective with irregular shaped and leaky vessels and have thickened membranes. The vessels also have dead ends and an insufficient number of pericytes to maintain the stability of the vessel. Blood vessels in tumors also have constricted and/or wide areas that add to the poor blood circulation. In the interstitial space of the tumor, there is a denser network of collagen fibers and an increase number of fibroblasts to make the tissue more rigid and dense. More macrophages and other inflammatory cells exist in tumors than normal tissue which release cytokines and growth factors that increase IFP by acting on blood vessels and stroma fibroblasts. Tumors often lack lymph vessels which are responsible for lowering IFP by removing soluble proteins and interstitial fluid.

The raised IFP caused by the above described ailments make it difficult to treat the tumors due to the poor uptake and circulation. Studies have also shown that lowering the IFP of tumors can increase circulation and drug uptake. Thus a lowered IFP creates a "window of opportunity" for increasing the efficacy of chemotherapy. Through stabilizing the blood vessels and increasing circulation, the IFP can be lowered to normal levels allowing the chemotherapy to better diffuse into the tumor tissue. To increase the efficiency, the IFP of the tumor should be continuously measured to insure that the chemotherapy is administered when the IFP is at its lowest.

Unfortunately, the current established methods require a clinical setting and an invasive procedure. Continuous monitoring can be cumbersome and can result in the patient lying immobile to avoid damaging the sensor, affecting the pressure measurements, and injuring himself/herself during the procedure. Wireless pressure sensors (active and passive) have recently been developed to measure pressures in vivo without the need of an invasive procedure to record a pressure measurement. While these devices are biocompatible and can wirelessly record pressure measurement, they would not fit the parameters for wirelessly measuring IFP inside of tumors. The devices either have membranes that would be exposed to the solid tissue or are too large to be implanted inside of a tumor or interstitial space. Continuous monitoring of IFP with a wireless implantable sensor can open up new opportunities in clinical practice where a therapeutic agent can be administered at the right time frame when the IFP is at its lowest. However, the currently available IFP measurement methods and systems do not lend themselves to such continuous and/or chronic monitoring of IFP.

Accordingly, there is an unmet need for wireless pressure sensors that can non-invasively and continuously measure IFP, making improved delivery of therapeutic agents to tumors possible during the "window of opportunity" when IFP is relatively lower.

SUMMARY

A system for a wireless implantable pressure sensor is disclosed. The system includes an energization/interrogation arrangement configured to generate an energization signal and to receive and interrogate a response signal, and an implantable pressure sensor arrangement. The arrangement includes a substrate, a coil positioned on the substrate, a flexible membrane positioned proximate to the coil and configured to be moveable with respect to the coil, thereby forming a fluid chamber, fluidly sealed from outside of the implantable pressure sensor arrangement, a porous membrane positioned on the flexible membrane and configured to transfer pressure from outside of the implantable pressure sensor arrangement onto the flexible membrane wherein a differential pressure is generated on the two sides of the flexible membrane thereby causing the flexible membrane to deflect towards and away from the coil, and an electrode coupled to the flexible membrane. The movement of the flexible membrane with respect to the coil is configured to change the resonant frequency of the implantable pressure sensor arrangement, the change readable by the energization/interrogation arrangement as a function of pressure existing outside of the implantable pressure sensor arrangement.

An implantable pressure sensor arrangement is disclosed. The arrangement includes a substrate, a coil positioned on the substrate, a flexible membrane positioned proximate to the coil and configured to be moveable with respect to the coil, thereby forming a fluid chamber, fluidly sealed from outside of the implantable pressure sensor arrangement, a porous membrane positioned on the flexible membrane and configured to transfer pressure from outside of the implantable pressure sensor arrangement onto the flexible membrane wherein a differential pressure is generated on the two sides of the flexible membrane thereby causing the flexible membrane to deflect towards and away from the coil, and an electrode coupled to the flexible membrane. The movement of the flexible membrane with respect to the coil configured to change resonant frequency of the implantable pressure sensor arrangement, the change is readable by an energization/interrogation arrangement as a function of pressure existing outside of the implantable pressure sensor arrangement.

BRIEF DESCRIPTION OF DRAWINGS

While some of the figures shown herein may have been generated from scaled drawings or from photographs that are scalable, it is understood that such relative scaling within a figure are by way of example, and are not to be construed as limiting.

FIGS. 7(a1)-7(e) are exemplary schematic representation of a fabrication process for the wireless IFP sensor of FIG. 1.

DETAILED DESCRIPTION

For the purposes of promoting an understanding of the principles of the disclosure, reference will now be made to the embodiments illustrated in the drawings and specific language will be used to describe the same. It will nevertheless be understood that no limitation of the scope of the disclosure is thereby intended, such alterations and further modifications in the illustrated device, and such further applications of the principles of the disclosure as illustrated therein being contemplated as would normally occur to one skilled in the art to which the disclosure relates.

Figure 1:
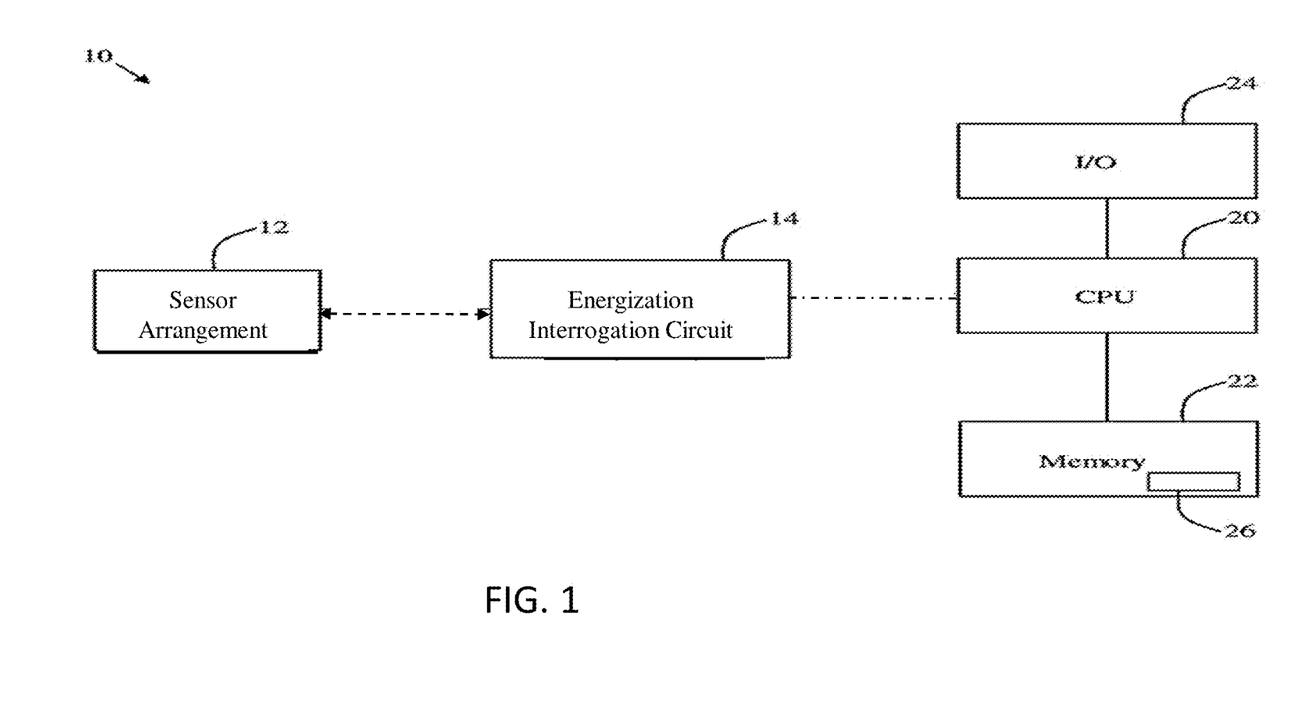
FIG. 1 is a block diagram of an exemplary system for energization and interrogation of a wireless interstitial fluid pressure (IFP) sensor arrangement, according to the present disclosure.

FIG. 1 is a block diagram of an exemplary system for energization and interrogation of an interstitial fluid pressure (IFP) sensor arrangement, according to the present disclosure. In this description the interstitial pressure sensor arrangement of this disclosure is also interchangeably referred to as a pressure sensor or simply a sensor. The system 10 includes a sensor arrangement 12 (also referred to as the wireless IFP sensor arrangement), an energization-interrogation circuit block 14, a processing circuit 20, a memory block 22 and an input/output (I/O) device 24. The I/O device 24 may include a user interface, graphical user interface, keyboards, pointing devices, remote and/or local communication links, displays, and other devices that allow externally generated information to be provided to the system 10, and that allow internal information of the system 10 to be communicated externally.

The processing circuit 20 may suitably be a general purpose computer processing circuit such as a microprocessor and its associated circuitry. The memory block 22 may suitably be various memory and data storage elements associated with a general purpose computer. Within the memory block 22 are various instructions in a program instruction block 26 within the memory block 22. The processing circuit 20 is configured to execute the program instructions 26 to carry out the various operations.

The processing circuit is also connected to the I/O device 24 to receive data from, and present data to a user. The processing circuit 20 is also connected to the energization-interrogation circuit block 14 to receive data from, and send data to, the energization-interrogation circuit block 14. This connection is shown in dashed lines to indicate that the connection can be a wired connection or a wireless connection, including a cellular, radio frequency-based, Bluetooth-based, or based on any other wireless communication protocol known to a person having ordinary skill in the art. The data communicated between the processing circuit 20 and the energization-interrogation circuit block 14 includes the energization signal as well as the readout data (also referred to herein as the interrogation data).

The memory block 22 may include random access memory (RAM), read only memory (ROM), programmable read only memory (PROM), erasable programmable read only memory (EPROM), or electrically erasable read only memory (EEPROM), and other types of memory known in the art suitable for storing data. The data may be of the type that continuously changes, or of the type that changes during operations of the energization-interrogation circuit block 14.

It should be appreciated that while only one sensor arrangement 12 is depicted in FIG. 1, multiple sensors can be combined to provide a network of sensors in the system 10. Each of these sensors is coupled to the energization and interrogation circuit 14 via a networked connection, e.g., a multiplexer. The network connection between the Sensor Arrangement 12 and the enrgization-interrogation circuit 14 is shown in dashed line to indicate the connectivity can be wireless.

In the present disclosure various embodiments of wirelessly measuring IFP wirelessly are presented. These embodiments include pressure sensors and methods of interrogating and receiving response signals to infer the IFP. Also disclosed in this disclosure are configurations and fabrication of wireless pressure sensors capable of monitoring IFP continuously.

Figure 2:
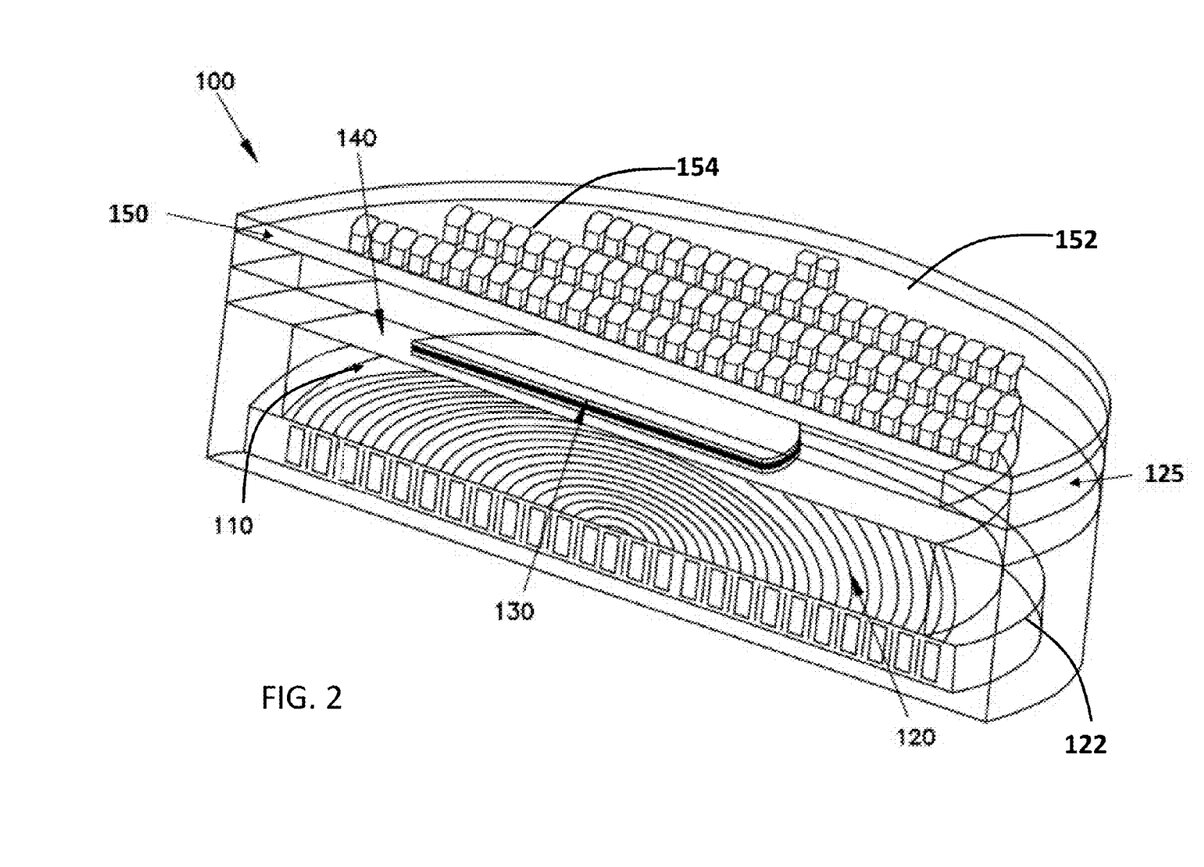
FIG. 2 is a perspective schematic representation of a wireless IFP sensor of FIG. 1 with a Guyton Chamber.

In the present disclosure a Guyton chamber is integrated with a wireless pressure sensor. A Guyton chamber includes a perforated capsule implanted subcutaneously into a desired interstitial tissue where the IFP is to be measured. Such a chamber allows IFP measurement by permitting the interstitial liquid to impart the interstitial pressure. Previous uses of a Guyton chamber included invasive methods to measure the IFP, once the Guyton chamber has been implanted. FIG. 2 is a perspective schematic representation of an inductive wireless IFP sensor with an integrated Guyton Chamber. In FIG. 2, the wireless sensor IFP sensor 100 includes a fluid chamber 110. The fluid chamber 110 can be formed by utilizing polydimethylsiloxane (PDMS), silicone, or other suitable material. The fluid chamber 110 is formed by the space between a planar coil 120 and a thin electrically conductive plate 130. The fluid chamber 110 can be filled with air or other compressible fluids. The thin electrically conductive plate 130 can be made from nickel-plated copper, or other suitable electrically conductive and/or ferromagnetic material. The planar coil 120 can be made of copper or other similar metals or alloys. As a non-limiting example, the planar coil is about 5 mm in diameter, about 250 microns thick and is embedded in a biocompatible material 122, such as polyimide, to ensure its biocompatibility. The electrically conductive plate 130 is embedded in a flexible membrane 140. A rigid perforated membrane 150 including a solid portion 152 and a perforated portion 154 is disposed proximate to the flexible membrane 140 forming a Guyton chamber 125 between the perforated membrane 150 and the flexible membrane 140. The Guyton chamber 125 can be filled with a non-compressible fluid or allow interstitial fluid in to fill the Guyton chamber 125 in order to translate pressure existing in the interstitial fluid to be directly applied to the flexible membrane 140. In one respect, the Guyton chamber 125 also protects the flexible membrane 140 from physical pressure caused by solid tissue.

The flexible membrane 140 can be made from a flexible material, such as silicone or other suitable material. Such suitable materials for the flexible membrane 140 possess a low Young's modulus in the range of 40-60 kPa. For example, ECOFLEX has a Young's modulus of 55.2 kPa and has the ability to stretch up to 800%. While this range is given as an example, other values for Young's modulus can be chosen to obtain the desired sensitivity and range of measurement of deflection of the flexible membrane 140 which has the nickel-plated copper plate 130 embedded in it. Since the electrically conductive plate 130 moves with the flexible membrane 140, the lower the Young's modulus of the flexible membrane 140, the greater the distance by which the electrically conductive plate 130 can move.

In the IFP sensor 100, the combination of the electrically conductive plate 130 embedded in the flexible membrane 140 is at a variable distance away from the planar coil 120. In operation, the interstitial fluid at a pressure P1 exerts a force on the flexible membrane 140. The fluid chamber is at a pressure P2. If P1-P2 is a positive number, then the flexible membrane 140 moves the electrically conductive plate 130 closer to the planar coil 120. This movement of the flexible membrane 140 changes the resonant frequency of the sensor 100. Such a change in resonant frequency can be interrogated by the energization-interrogation circuit block 14 (FIG. 1). This resonant frequency therefore depends on the distance between the electrically conductive plate 130 and the planar coil 120, which in turn depends on the fluid pressure acting on the flexible membrane 140.

It should be noted that the relationship between the electrically conductive plate 130 and the coil 120 defines a capacitance between these two members. If the electrically conductive plate 130 is non-ferromagnetic, then changes in the relative spacing between these two (120 and 130), principally changes the capacitance of the sensor 100. If the material of the electrically conductive plate 130 is ferromagnetic, then changes in the relative spacing between these two (120 and 130), principally changes the inductance of the sensor 100. The latter can result in a higher sensitivity to changes in resonant frequency of the sensor 100.

It should be noted that the materials, dimensions, and properties noted above for the electrically conductive plate 130 and the planar coil 120 are by way of example only and a person having ordinary skill in the art will be able to substitute other materials and dimensions. Further, other choices can be chosen by those skilled in the art for the flexible membrane 140 and for the materials to embed the planar coil 120.

Figure 3:
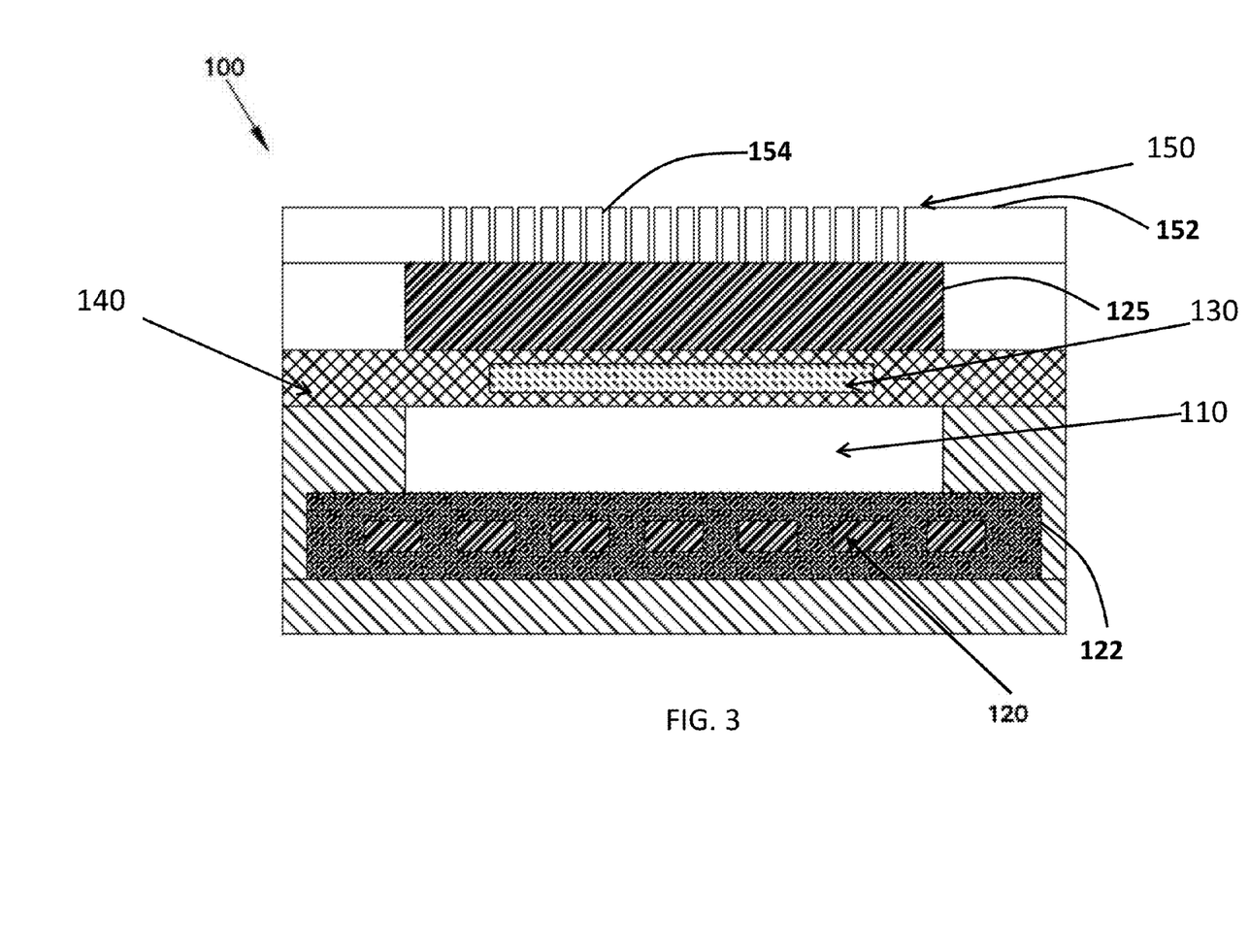
FIG. 3 is a schematic representation of the wireless IFP sensor of FIG. 1 when the interstitial pressure is in equilibrium with the surrounding fluids.

FIG. 3 is a schematic cross-sectional representation of the wireless IFP sensor 100 when the interstitial pressure is in equilibrium with the surrounding fluids. In this view, the interstitial fluid (not shown) moves through the perforations 154 and exerts a force to the flexible membrane 140. A non-limiting example for the size of the pores in the porous membrane is of the order of 100 micrometers. However, the pressure in the fluid chamber 110 is about the same as the interstitial fluid (not shown) and thus the flexible membrane remains in a non-deflected state.

Figure 4:
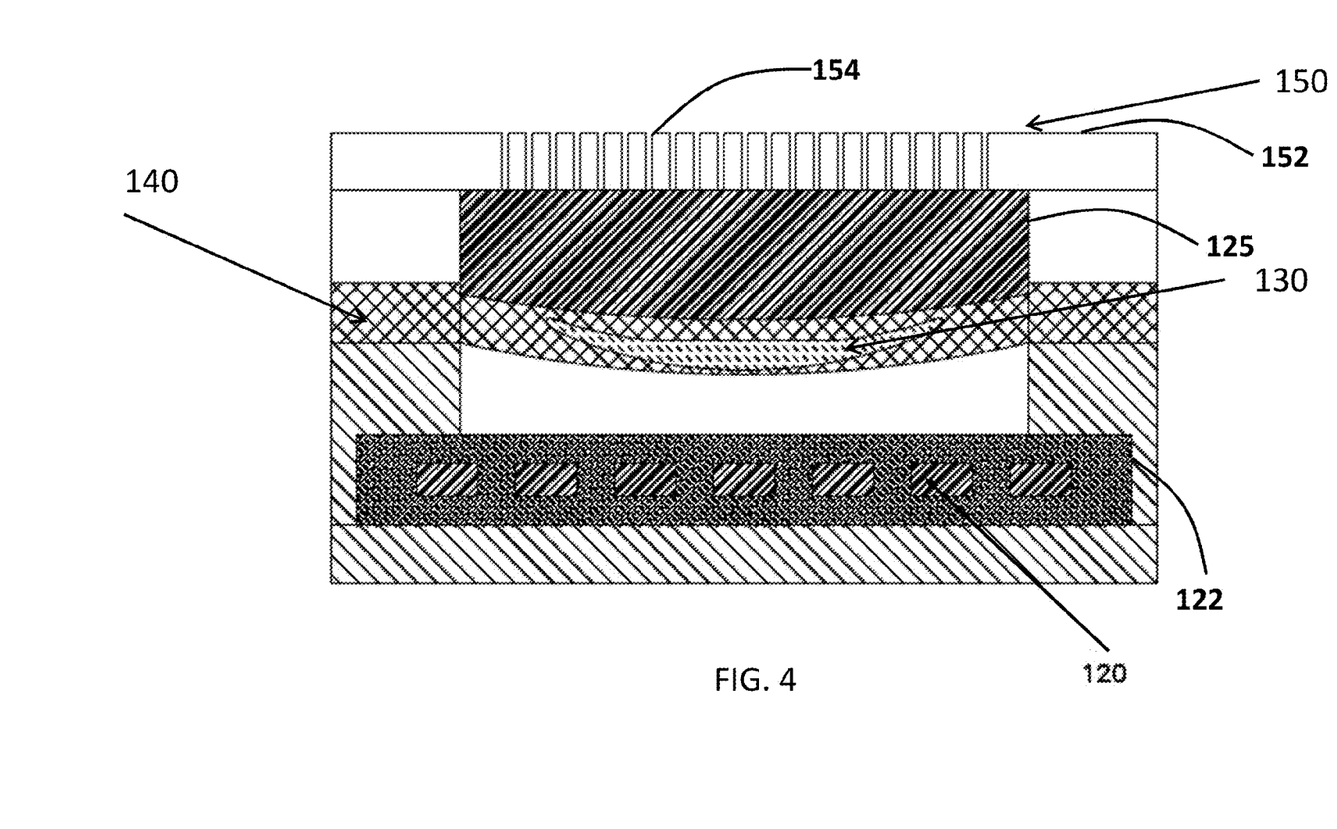
FIG. 4 is a schematic representation of the wireless IFP sensor of FIG. 1 when the interstitial pressure is higher than the pressure in surrounding fluids.

With a rise of interstitial pressure, the interstitial fluid (not shown) penetrates or exerts into or on to the Guyton chamber through the pores in the porous membrane 150 and applies a force to the flexible membrane 140 which has the electrically conductive plate 130 embedded in it. FIG. 4 shows the deflection of electrically conductive plate 130 which is embedded in the flexible membrane 140. It is this deflection that causes the change in resonant frequency. In response, the flexible membrane 140 deflects, moving the electrically conductive plate 130 closer to the planar coil 120. The result is a change in the sensor's resonant frequency which can then be detected by a phase-dip method using an external readout coil (not shown).

Two primary design parameters of the sensor are sensitivity and dynamic range. The sensor's resonant frequency is modulated by the deflection of the flexible membrane 140 with the electrically conductive plate 130 embedded in it. The flexible membrane 140 can be modeled as a uniformly loaded circular plate under large deflections, with the center deflection given by:

$$w_o = 0.662 a^3 \sqrt{\frac{a \Delta P}{Eh}} \quad (1)$$

where, E is the Young's modulus,
h is the membrane thickness,
a is the membrane radius, and
$\Delta P$ is the applied pressure ($\Delta P = P_{out} - P_{in}$). Substituting into $w_o$ and solving for the external pressure, $P_{out}$;

$$P_{out} = \left(\frac{w_o}{0.662}\right)^3 \frac{Eh}{a^4} + P_{in} \quad (2)$$

The internal pressure ($P_{in}$) of the fluid chamber 110 can be calculated by using the ideal gas law (for where the fluid chamber 110 is filled with air or other fluids that can be modeled as ideal gases), resulting in:

$$P_{in} = \frac{mR_{air}T}{V_o - \frac{\pi}{3}w_o a^2} \quad (3)$$

where m is the mass of air in chamber,
R<sub>air</sub> is the gas constant for air,
T is the temperature, and
V<sub>o</sub> is the original volume of chamber. Substituting Equation (3) into (2), one obtains a relationship between the deflection of membrane 140 and the pressure external to the Guyton chamber external as a function of various sensor parameters as shown in Equation (4) below:

$$P_{out} = \left(\frac{w_o}{0.662}\right)^3 \frac{Eh}{a^4} + \frac{mR_{air}T}{V_o - \frac{\pi}{3}w_o a^2} \quad (4)$$

Figure 5:
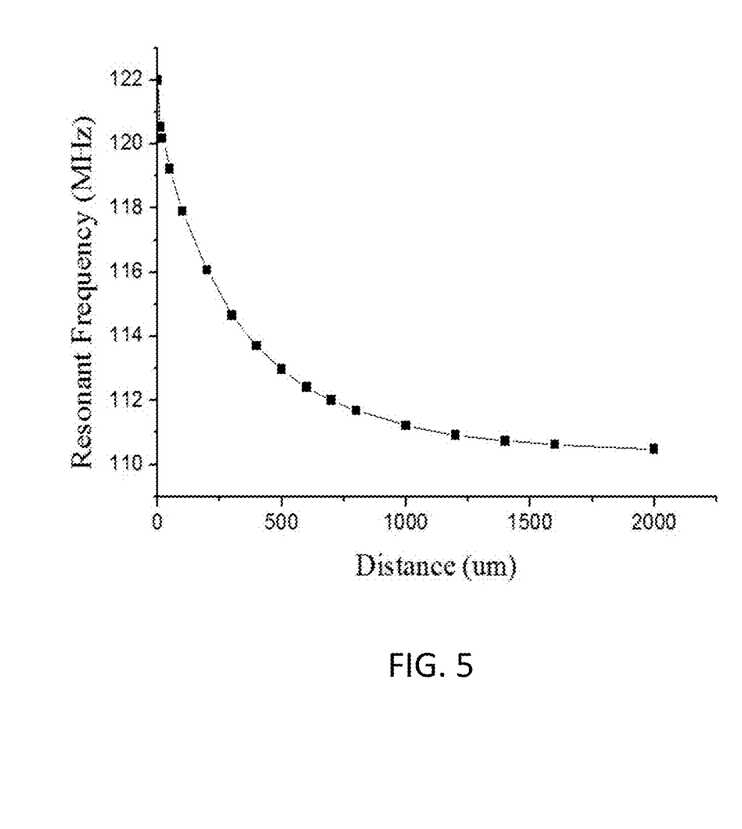
FIG. 5 is a plot of resonant frequency vs. distance of a nickel-plated copper plate as part of a coil.

Another design parameter is the resonant frequency as a function of the distance between the electrically conductive plate 130 and the coil 120. FIG. 5 is an experimental plot showing the resonant frequency for an electrically conductive plate 130 (2.5 mm diameter) embedded inside a 100 µm thick ECOFLEX at various distances from the coil 120; showing an increase in the resonant frequency as the electrically conductive plate 130 moves closer to the coil 120. This behavior can be explained by the saturation of magnetic flux density of the magnetic material of the electrically conductive plate 130 (20 to 100 A/M). Equation (5) shows the total magnetic energy stored in the device:

$$U = \int_{air} \frac{B^2}{2\mu_0} \cdot dV + \int_{nickel} \frac{B_s^2}{2\mu_0} \cdot dV = \frac{1}{2} Li^2 \quad (5)$$

where, i is the current, and
B<sub>s</sub> is the saturation magnetic flux density (constant) in the magnetic material of the electrically conductive plate 130. As the electrically conductive plate 130 moves closer to the coil 120, the strength of the magnetic field increases until the magnetic flux in the electrically conductive plate 130 is saturated. After saturation, any change in the total magnetic energy is a result of changes in the magnetic energy stored in air (the second term of equation (5) is constant). This results in a net loss in total magnetic energy and accompanied reduction in inductance value. The resonant frequency of an LC system can be expressed in terms of the total magnetic energy, U, as:

$$f_0 = \frac{1}{2\pi\sqrt{L \cdot C}} = \frac{1}{2\pi\sqrt{\frac{2 \cdot U}{i^2} \cdot C}} = \frac{1}{2\pi \cdot k \cdot \sqrt{U}} \quad (6)$$

where, C is the capacitance of the sensor, and
k is a constant.

Figure 6:
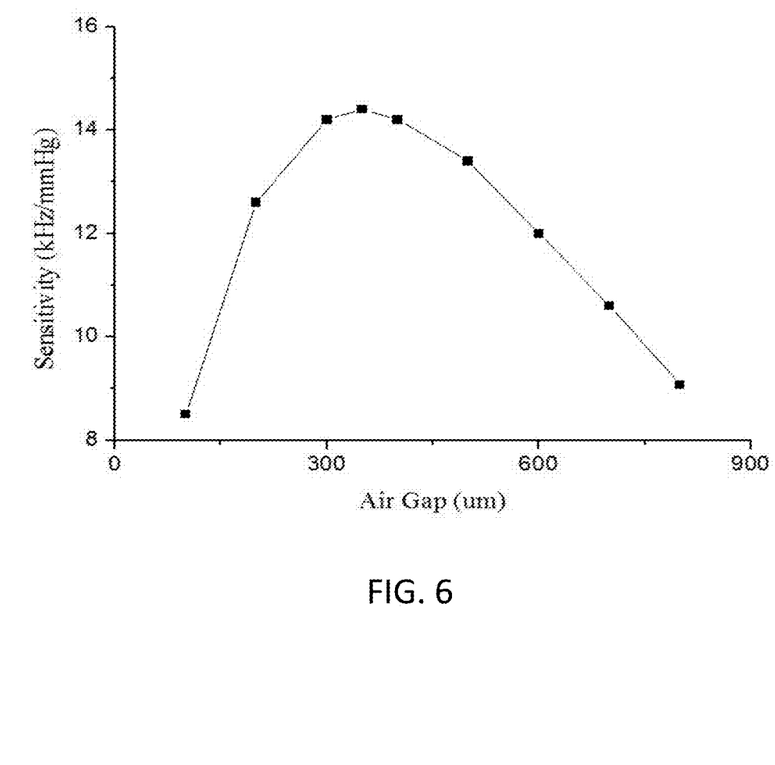
FIG. 6 is a plot of calculated sensitivity for different air gap values in the wireless IFP sensor of FIG. 1.

FIG. 6 is a plot of sensitivity of resonance frequency vs. distance of the electrically conductive plate 130 from the coil 120. Referring to FIG. 6, when the electrically conductive plate 130 is about 400 micrometers from the coil 120, the resonant frequency is at its highest sensitivity to changes in the distance between the electrically conductive plate 130 and the coil 120. Sensitivity is defined as resonant frequency for 1 mm of Hg pressure in the Guyton chamber 125. Thus, a diameter of 5 mm and a gap of 400 µm between the electrically conductive plate 130 and the planar coil 120 were chosen for fabricating a prototype. This gap is small enough to maintain the overall small dimensions of the sensor while providing a sufficiently high sensitivity at appropriate dynamic range (−6 to 30 mmHg).

Figure 7:
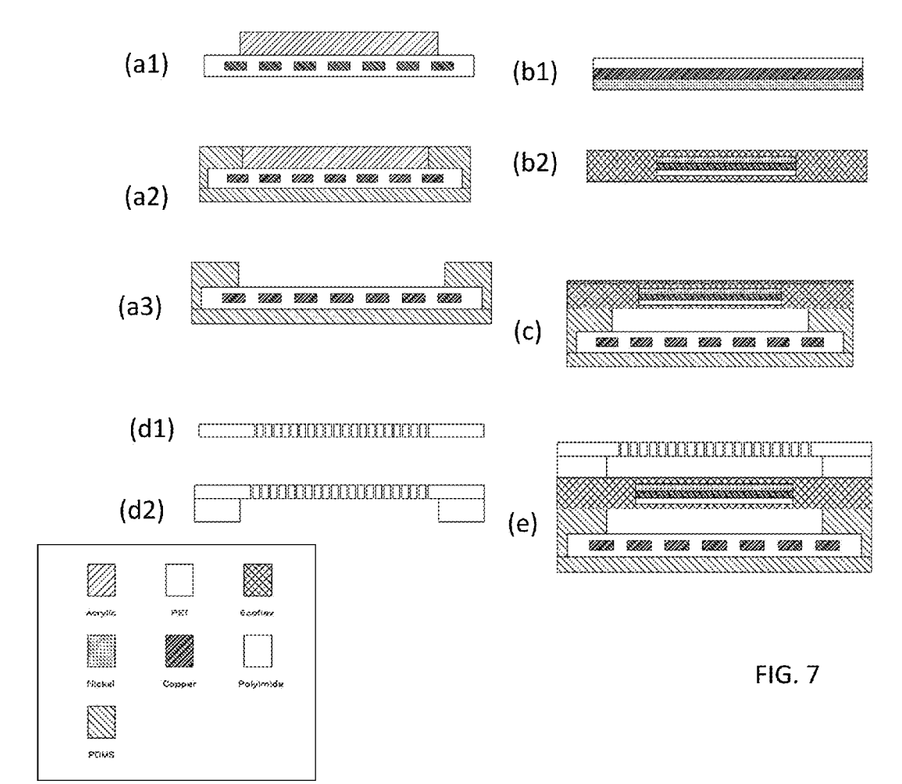

FIG. 7 shows a fabrication process for the sensor according to the present disclosure. The sensor principally includes three parts: a coil, a membrane in which the electrically conductive plate is embedded, and a Guyton chamber. First, a polyimide (PI) based double-layer planar coil was fabricated (PARLEX). The coil is 5 mm in diameter and 250 µm in thickness (12-turns; 100 µm trace/spacing). A laser machined acrylic disk (5 mm O.D., 380 µm thick) is temporarily attached to the top of the coil as a mold for making the fluid chamber 110 (FIG. 7, a1). The coil and acrylic ring were then encapsulated with PDMS (FIG. 7, a2) and allowed to cure. Next, the acrylic disk was removed to reveal the air chamber (FIG. 7, a3). Next, a polyimide-laminated copper sheet (25 µm thick) is coated with nickel (30 µm thick) using an electroless plating solution (CASWELL) and cut to a diameter of 2.5 mm (FIG. 7, b1). The plate is then embedded into an ECOFLEX membrane (100 µm thick) (FIG. 7, b2). Once cured, the membrane is cut and bonded to the PDMS-embedded coil using air plasma bonding to seal off the air chamber (FIG. 7, c). Finally, the Guyton capsule is fabricated out of PET transparent film. A porous membrane is made by laser machining 120 µm-diameter holes into a PET film (FIG. 7, d1), and is then bonded to a laser-machined PET film annulus using UV-curable adhesive (LOCTITE) (FIG. 7, d2). The Guyton capsule is bonded to the top of the ECOFLEX membrane using a thin layer of clear silicone adhesive (DAP PRODUCT) and left to fully cure for 24 hours to create the cavity inside the capsule and finalize the pressure sensor (FIG. 7, e).

Figure 8:
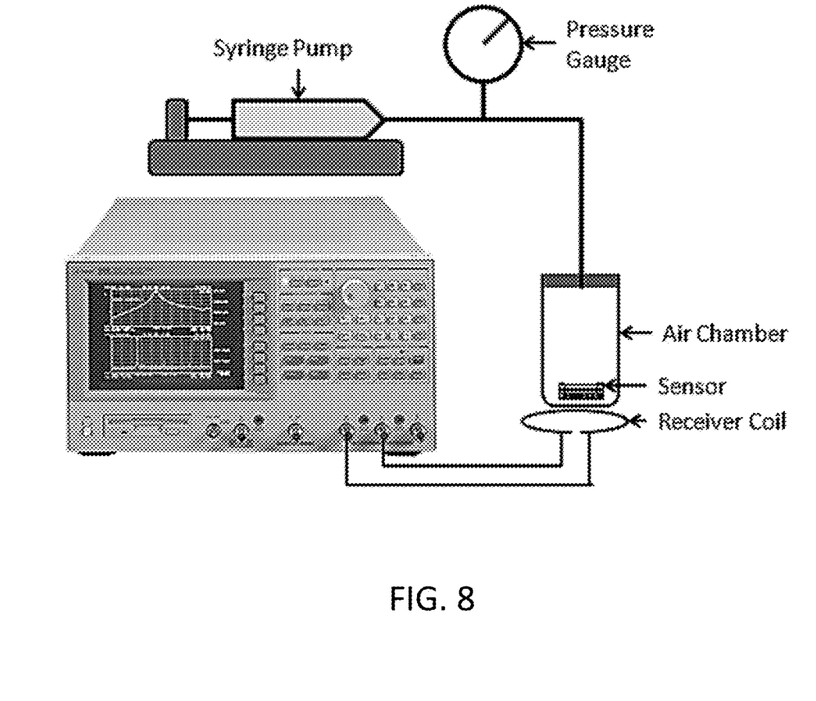
FIG. 8 is a sensor characterization set up for the wireless IFP sensor of FIG. 1.

FIG. 8 shows an exemplary set up utilized for the characterization of a sensor according to the present disclosure. The sensor was placed in a sealed chamber connected to a syringe pump and a pressure gauge. A receiver coil was connected to a network analyzer and was placed 3 mm away from the sensor. When air was pumped into the chamber, the pressure inside increased and the resonant frequency of the sensor was shifted. The resonant frequency was measured by a phase-dip method utilizing.

Figure 9:
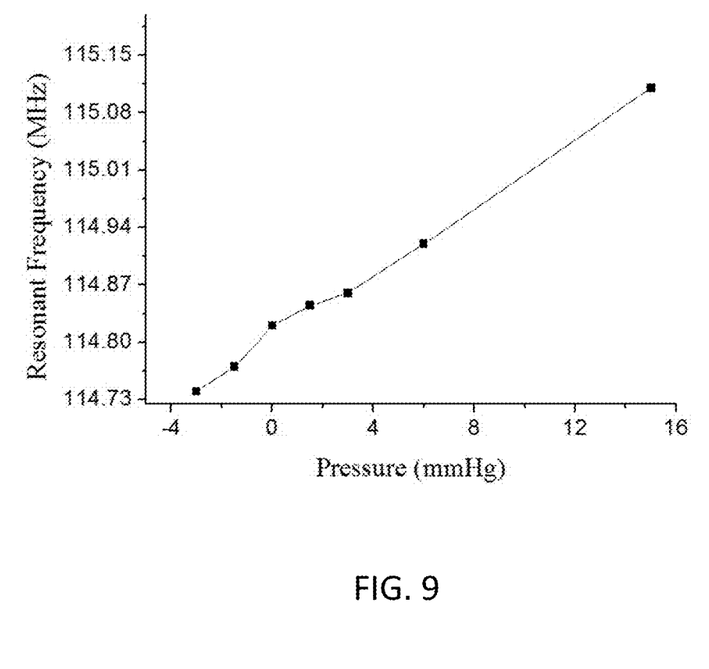
FIG. 9 is a plot of resonant frequency vs. exerted pressure for the wireless IFP sensor of FIG. 1.

FIG. 9 shows the resonant frequency of the fabricated sensor in response to external pressure. The sensor's resonant frequency increases when the electrically conductive plate 130 moves closer to the sensor coil 120 in response to an increase in interstitial fluid pressure. The sensitivity of the sensor was measured to be around 20 kHz/mmHg.

To test the sensors in vivo, IFP sensors were fabricated and implanted into the human breast cancer tumor grown on nude mice. After two weeks from the implantation to allow the tissues to heal from the implantation, the interstitial fluid pressures were monitored for 12 days. The mice were not sedated and were held still and the receiver coil was brought close to the implantation site to make the measurement. The mice were split into two groups with one group receiving angiogenesis inhibitor and the other receiving saline injection at the day 5. After 12 days of monitoring, the sensor's functionality was verified by changing the interstitial fluid pressure by injecting phosphate-buffered saline, PBS, (0.9% NaCl, for example) into the tumors to apply hydrostatic pressure. A fiber optics pressure sensor was inserted into the tumor using the wick-in-needle technique using a 25 gauge needle to be used as a reference. The pressure inside of the tumors increased and decreased within minutes of injection and the pressure readings from the implanted sensor and the fiber optics systems were both recorded.

The experiments showed a shifting of the resonant frequency of the sensor in response to the applied pressure in the saline chamber. As the pressure inside of the chamber increased, an increase in the resonant frequency was observed. The sensor displayed a linear response over the range of −10 to 15 mmHg with a sensitivity of 60 kHz/mmHg with a resolution of 1 mmHg (S.E. of 40 kHz).

The sensor's resonant frequencies during PBS injections experiment were monitored. It has been noted, due to the high permeability of the tumor vasculature and lack of lymphatic system, that the tumor IFP is uniform at the tumor core. After the PBS injection, the tumor fluidic pressure immediately increased and it was verified with the fiber optics pressure sensor. The sensor's resonant frequency increased. The pressure changes due to the PBS injections were almost instantaneous. After the second injection, due to the multiple punctures, the pressure inside the tumor dropped rapidly as the fluid was leaking out of the tumor. Within a minute, the tumor pressure reverted to its pressure baseline of about 5 mmHg. The pressure readings from the fiber optics reading and the IFP sensor matched closely according to the resonant frequency-pressure relationship of the sensor. The sensor showed a linear response inside of the tumor to the hydrostatic pressure applied through PBS injection. After the mice were sacrificed, the sensors were extracted from the tumors and examined and tested; the sensors retained its functionality and were structurally intact. There were no noticeable tissues residues or formations inside of the Guyton chamber confirming that the Guyton chamber can insulate the sensor from the tissue pressure.

While the present disclosure has been described with reference to certain embodiments, it will be apparent to those of ordinary skill in the art that other embodiments and implementations are possible that are within the scope of the present disclosure without departing from the spirit and scope of the present disclosure. It is therefore intended that the foregoing detailed description be regarded as illustrative rather than limiting. Thus this disclosure is limited only by the following claims.

The invention claimed is:

1. A system for a wireless implantable pressure sensor, comprising:
an energization/interrogation arrangement configured to generate an energization signal and to receive and interrogate a response signal; and
an implantable pressure sensor arrangement wirelessly coupled to the energization/interrogation arrangement, the implantable pressure sensor arrangement including:
a substrate,
a coil disposed on the substrate,
a flexible membrane disposed proximate to the coil and configured to be moveable with respect to the coil, thereby forming a fluid chamber fluidly sealed from outside of the implantable pressure sensor arrangement,
a porous membrane disposed on the flexible membrane and configured to transfer pressure from outside of the implantable pressure sensor arrangement onto the flexible membrane wherein a differential pressure is generated on the two sides of the flexible membrane, wherein the flexible membrane is configured to deflect toward or away from the coil, the porous membrane comprising a plurality of perforations, and wherein the porous membrane is configured to transfer fluid through each perforation of the plurality of perforations, wherein an entirety of the porous membrane is over the flexible membrane, and
an electrode coupled to the flexible membrane,
the movement of the flexible membrane with respect to the coil configured to change resonant frequency of the implantable pressure sensor arrangement, the change readable by the energization/interrogation arrangement as a function of pressure existing outside of the implantable pressure sensor arrangement.

2. The wireless implantable pressure sensor system of claim 1, the electrode is fixed to the flexible membrane.

3. The wireless implantable pressure sensor system of claim 2, the electrode is embedded in the flexible membrane.

4. The wireless implantable pressure sensor system of claim 1, the electrode is ferromagnetic.

5. The wireless implantable pressure sensor system of claim 4, the electrode is a nickel-plated copper plate.

6. The wireless implantable pressure sensor system of claim 1, the coil is copper.

7. The wireless implantable pressure sensor system of claim 1, the substrate is Polydimethylsiloxane.

8. The wireless implantable pressure sensor system of claim 1, the porous membrane is poly(ethylene terephthalate).

9. The wireless implantable pressure sensor system of claim 1, the fluid chamber includes compressible fluid.

10. The wireless implantable pressure sensor system of claim 9, the fluid chamber includes air.

11. The wireless implantable pressure sensor system of claim 1, the system configured to sense pressure in vivo.

12. The wireless implantable pressure sensor system of claim 11, the system configured to sense pressure inside a tumor.

13. An implantable pressure sensor arrangement, comprising:
a substrate;
a coil disposed on the substrate;
a flexible membrane directly over the coil and configured to be moveable with respect to the coil, thereby forming a fluid chamber, fluidly sealed from outside of the implantable pressure sensor arrangement;
a porous membrane disposed on the flexible membrane and configured to transfer pressure from outside of the implantable pressure sensor arrangement onto the flexible membrane wherein a differential pressure is generated on the two sides of the flexible membrane thereby causing the flexible membrane to deflect towards and away from the coil wherein an entirety of the porous membrane is over the flexible membrane; and
an electrode coupled to the flexible membrane,
the movement of the flexible membrane with respect to the coil configured to change resonant frequency of the implantable pressure sensor arrangement, the change readable by an energization/interrogation arrangement as a function of pressure existing outside of the implantable pressure sensor arrangement.

14. The implantable pressure sensor arrangement of claim 13, the electrode is fixed to the flexible membrane.

15. The implantable pressure sensor arrangement of claim 14, the electrode is embedded in the flexible membrane.

16. The implantable pressure sensor arrangement of claim 13, the electrode is ferromagnetic.

17. The implantable pressure sensor arrangement of claim 16, the electrode is a nickel-plated copper plate.

18. The implantable pressure sensor arrangement of claim 13, the coil is copper.

* * * * *